United States Patent
Taylor et al.

(10) Patent No.: US 9,713,533 B2
(45) Date of Patent: Jul. 25, 2017

(54) IN-LINE PEGGED HYBRID GLENOID

(71) Applicant: Biomet Manufacturing, LLC, Warsaw, IN (US)

(72) Inventors: Robert Taylor, Granger, IN (US); Benjamin I. Joseph, Fort Wayne, IN (US); Thomas M. Vanasse, South Bend, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 0 days.

(21) Appl. No.: 14/558,024

(22) Filed: Dec. 2, 2014

(65) Prior Publication Data

US 2016/0151164 A1    Jun. 2, 2016

(51) Int. Cl.
*A61F 2/40* (2006.01)
*A61F 2/30* (2006.01)

(52) U.S. Cl.
CPC ........ *A61F 2/4081* (2013.01); *A61F 2/30734* (2013.01); *A61F 2/30771* (2013.01); *A61F 2002/30013* (2013.01); *A61F 2002/3092* (2013.01); *A61F 2002/30405* (2013.01); *A61F 2002/30878* (2013.01); *A61F 2002/30881* (2013.01); *A61F 2002/30897* (2013.01); *A61F 2002/30904* (2013.01); *A61F 2310/00023* (2013.01)

(58) Field of Classification Search
CPC ...................... A61F 2/4081; A61F 2/40; A61F 2002/30878; A61F 2/30734; A61F 2002/30897
USPC ........................................... 623/19.11–19.13
See application file for complete search history.

(56) References Cited

U.S. PATENT DOCUMENTS

| 5,800,551 A | 9/1998 | Williamson et al. |
| 2007/0219638 A1* | 9/2007 | Jones .................... A61F 2/4081 623/19.11 |
| 2011/0035013 A1* | 2/2011 | Winslow ............... A61F 2/4003 623/19.13 |

(Continued)

FOREIGN PATENT DOCUMENTS

| EP | 2689751 A1 | 1/2014 | |
| FR | 2937245 B1 * | 4/2010 | ........... A61F 2/4081 |
| FR | 2971416 A1 | 8/2012 | |

(Continued)

OTHER PUBLICATIONS

"International Application Serial No. PCT/US2015/062070, International Search Report mailed Feb. 12, 2016", 4 pgs.

(Continued)

*Primary Examiner* — David H Willse
*Assistant Examiner* — Javier Blanco
(74) *Attorney, Agent, or Firm* — Schwegman Lundberg & Woessner, P.A.

(57) ABSTRACT

A glenoid implant can include a body, a first fixation member, a second fixation member, and a third fixation member. The body can include an articular surface and a scapula-engaging surface opposite from the articular surface. The first, second and third fixation members can extend from the scapula-engaging surface. The third fixation member can include a porous titanium material and be disposed between the first and second fixation members, such that the first, second and third fixation members define a substantially linear configuration.

5 Claims, 3 Drawing Sheets

(56) References Cited

U.S. PATENT DOCUMENTS

2013/0190881 A1   7/2013  Winslow et al.

FOREIGN PATENT DOCUMENTS

WO   WO-2015130006 A1   9/2015
WO   WO-2016089642 A1   6/2016

OTHER PUBLICATIONS

"International Application Serial No. PCT/US2015/062070, Written Opinion mailed Feb. 12, 2016", 7 pgs.
Walch, Giles, et al., "Morphological Study of the Glenoid in Primary Glenohumeral Osteoarthritis", The Journal of Arthroplasty, 14(6), (1999), 756-760.
Neer, Charles S., et al., "Glenoid Bone-Grafting in Total Shoulder Arthroplasty", The Journal of Bone and Joint Surgery, vol. 70-A, No. 8,, (Sep. 1998), pp. 1154-1162.

* cited by examiner

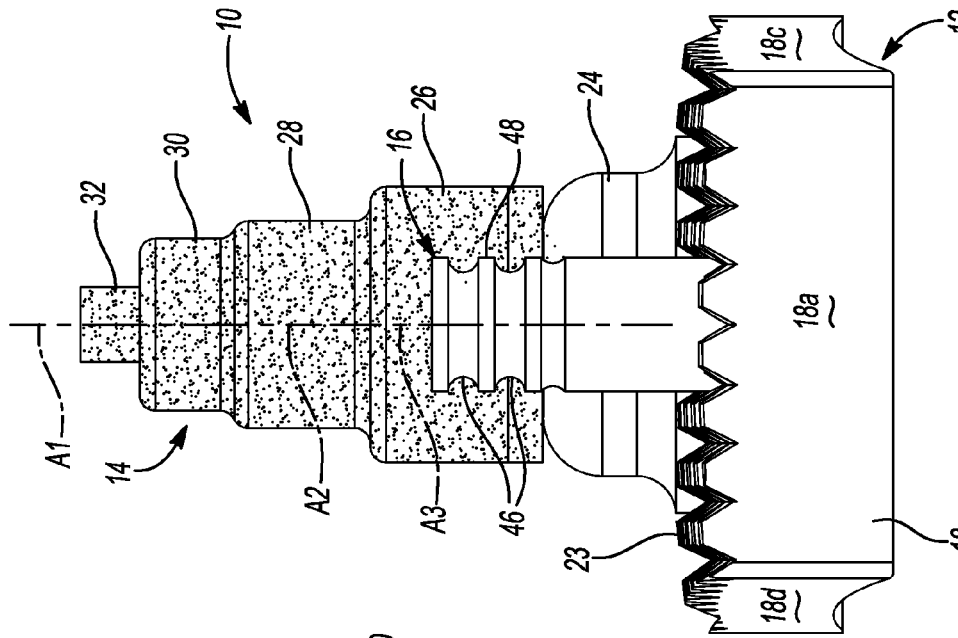
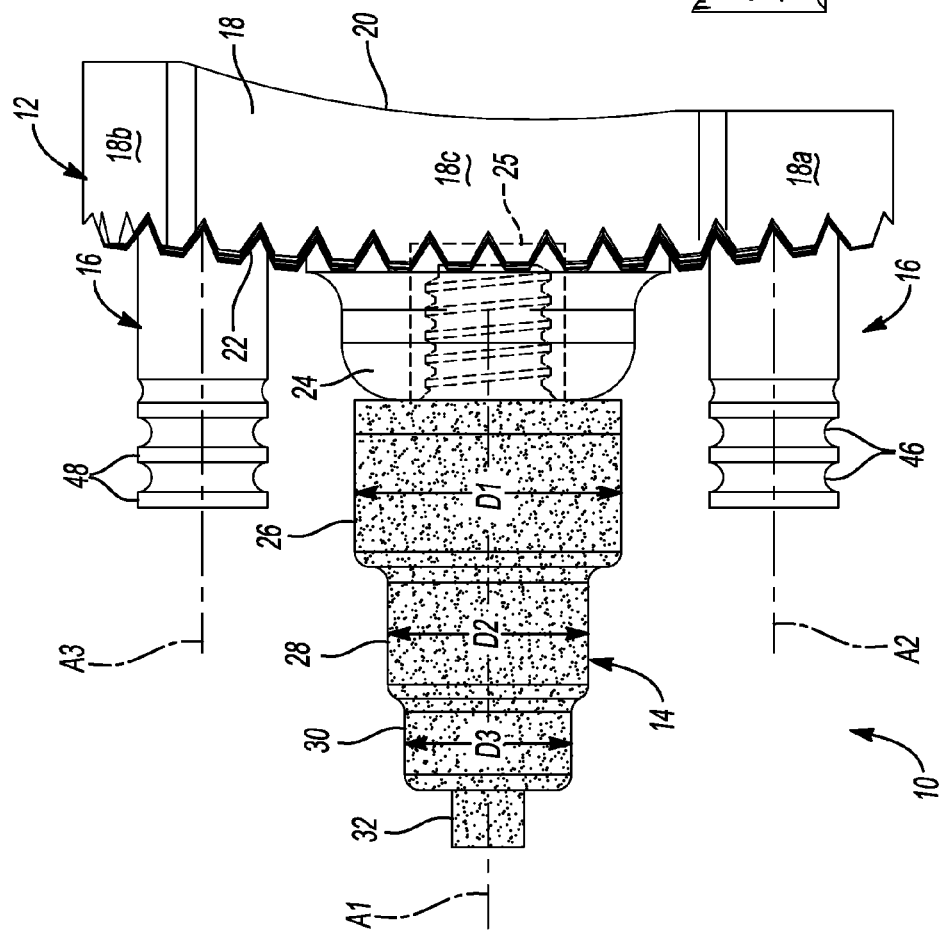

IN-LINE PEGGED HYBRID GLENOID

FIELD

The present disclosure relates to an implant, and more particularly to a device and method for securing a glenoid implant to a glenoid, including a glenoid having a narrow, or otherwise small, geometry.

BACKGROUND

This section provides background information related to the present disclosure and is not necessarily prior art.

Surgical procedures for repairing or reconstructing a joint may require securely fastening a surgical implant to a bone. For example, shoulder joint reconstruction may require fixing a glenoid implant to a scapula to reproduce or replicate a glenoid cavity on the scapula. In some situations, the glenoid cavity may present a narrow or otherwise small surface area, or other geometry, on which to secure the glenoid implant. The glenoid implant may include pegs distributed in a variety of configurations around the periphery of the implant. Corresponding holes may be formed in the scapula for receiving the pegs. In some configurations, the pegs may be received within the holes in a press-fit configuration. In addition, bone cement may be used to secure the pegs within the holes.

While known surgical implants have proven to be acceptable for their intended purposes, a continuous need for improvement in the relevant art remains.

SUMMARY

This section provides a general summary of the disclosure, and is not a comprehensive disclosure of its full scope or all of its features.

According to one particular aspect, the present disclosure provides a glenoid implant. The glenoid implant can include a body, a first fixation member, a second fixation member, and a third fixation member. The body can include an articular surface and a scapula-engaging surface opposite from the articular surface. The first, second and third fixation members can extend from the scapula-engaging surface. The third fixation member can include a porous titanium material and be disposed between the first and second fixation members, such that the first, second and third fixation members define a substantially linear configuration.

According to another particular aspect, the present disclosure provides an implant. The implant can include a body, a first fixation member and a second fixation member. The body can include an articular surface and a scapula-engaging surface opposite from the articular surface. The body can be at least partially formed from a first biocompatible material. The first and second fixation members can extend from a central portion of the scapula-engaging surface such that the first and second fixation members define an axis of symmetry relative to the scapula-engaging surface. At least one of the first and second fixation members can be formed from a second biocompatible material that is different than the first biocompatible material.

According to yet another particular aspect, the present disclosure provides a glenoid implant. The glenoid implant can include a body a first fixation member, a second fixation member, and a third fixation member. The body can include an articular surface and a scapula-engaging surface opposite from the articular surface. The body can be at least partially formed from a first biocompatible material. The first, second and third fixation member can extend from the scapula-engaging surface and be disposed in a central portion of the glenoid implant. The third fixation member can include a second biocompatible material different than the first biocompatible material.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 3 is a side view of the glenoid implant of FIG. 1;

FIG. 4 is a top view of the glenoid implant of FIG. 1; and

Corresponding reference numerals indicate corresponding parts throughout the several views of the drawings.

DETAILED DESCRIPTION

Figure 1:
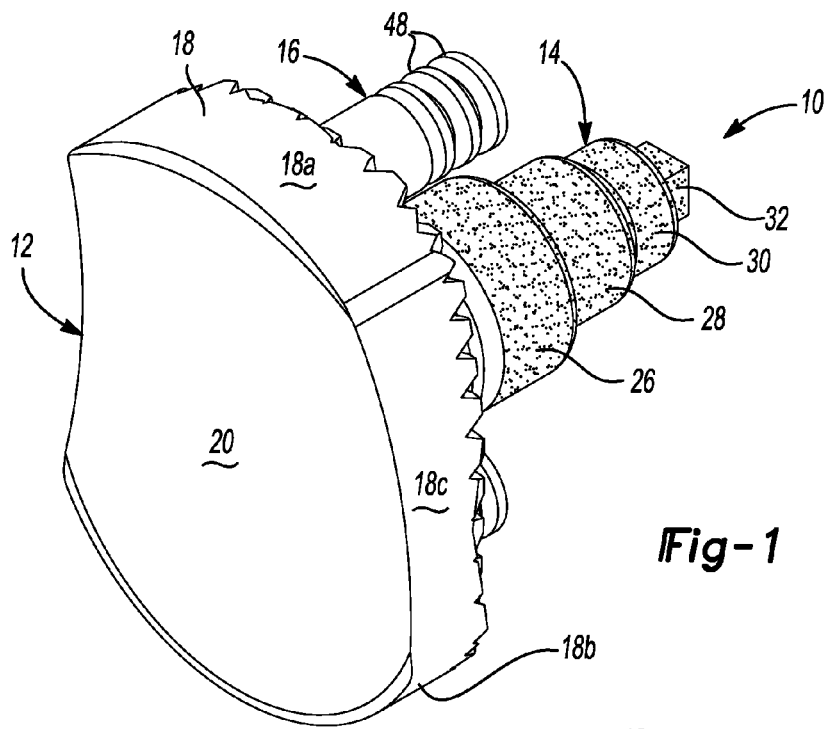
FIG. 1 is a first perspective view of a glenoid implant in accordance with the principles of the present disclosure.
Figure 2:
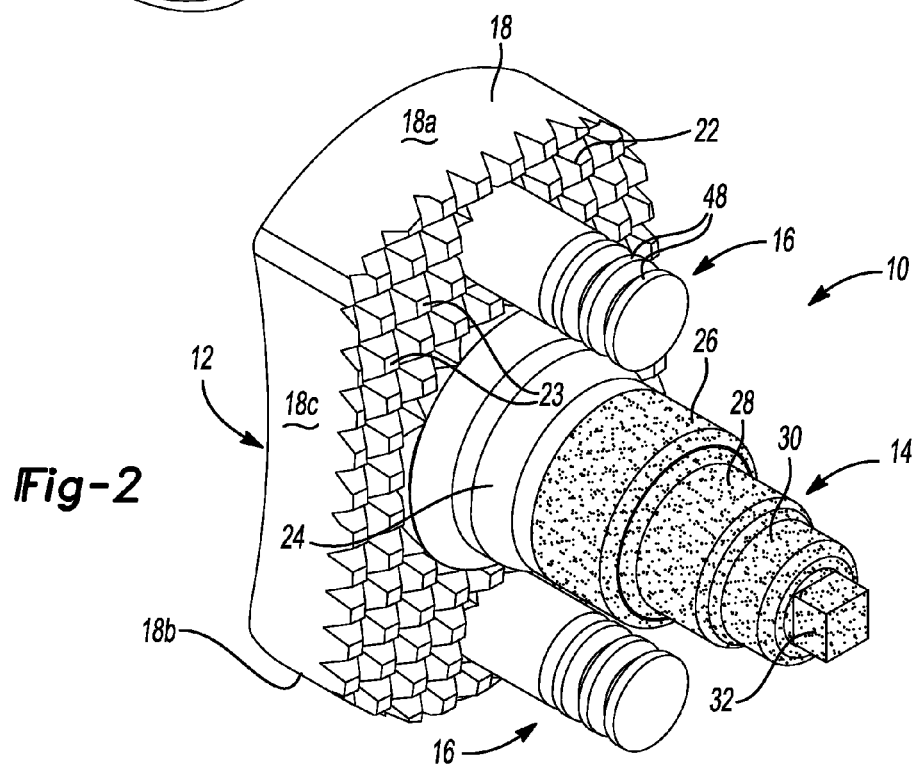
FIG. 2 is a second perspective view of the glenoid implant of FIG. 1.

Example embodiments will now be described more fully with reference to the accompanying drawings.

With general reference to FIGS. 1-5 of the drawings, an implant constructed in accordance with the principles of the present disclosure is illustrated and identified at reference character 10. According to one exemplary use, the implant 10 may be a glenoid implant for use in shoulder joint replacement. In such case, the glenoid implant can replace or replicate an entire glenoid cavity or a portion thereof for anatomic shoulder joint replacements. The glenoid implant can also fill a defect in the glenoid cavity such as a void due to severe wear. It will also be appreciated, however, that the present teachings may be adapted to fix various implants to various bones.

The implant 10 may generally include a body 12. The body 12 may be a generally rectangular body 12 having a pear-shaped outline (by way of non-limiting example), a central fixation member 14, and a pair of peripheral fixation members 16. The implant 10 can be formed from any biocompatible material, including, polymer, ceramic, metal or combinations thereof. In some configurations, the body 12 and/or the peripheral fixation members 16 may be formed from a polyethylene material such as an ultrahigh molecular weight polyethylene or a highly cross-linked polyethylene. The body 12 and/or the peripheral fixation members 16 may also include, via doping, blending, infusion or another suitable process for combining materials, an antioxidant, such as E1®, commercially available from Biomet Manufacturing Corporation®, for example.

The implant 10, including at least the body 12 and the peripheral fixation members 16, can be formed using any suitable manufacturing technique, including machining, direct compression molding and/or additive manufacturing which enables forming multiple implants in a single build and decreases manufacturing time. Once formed, the implant 10 can be further processed (e.g., polished, blasted, machining) as desired. For example, the implant 10 can be polished for articulation with a humeral head made from polyethylene or another suitable material. Alternatively, polyethylene can be molded over or pressed onto the body 12 for articulation with a metal humeral head.

The body 12 may be substantially similar to the "body 12" shown and described in commonly-owned U.S. patent application Ser. No. 14/095,565 filed Dec. 3, 2013 and entitled "Patient-Specific Glenoid Implant", which is hereby incorporated by reference in its entirety. In this regard, the body 12 extends along a central longitudinal axis A (FIG. 5) and has a peripheral surface 18, an articular surface 20, and a scapula-engaging surface 22 opposite from the articular surface 20. The peripheral surface 18 includes superior and inferior portions 18a, 18b that are rounded (e.g., convex), and anterior and posterior portions 18c, 18d that are flat or slightly rounded (e.g., concave). The peripheral surface 18 can be patient-specific and can match or replicate a peripheral surface of a glenoid cavity of a specific patient. The central fixation member 14 and the peripheral fixation members 16 extend from the scapula-engaging surface 22 of the body 12. In this regard, the central fixation member 14 may extend from the scapula-engaging surface 22 along a first central axis A1, while the peripheral fixation members 16 may extend from the scapula-engaging surface 22 along second and third central axes A2, A3, respectively. Although the implant 10 is shown with two peripheral fixation members 16, the implant 10 can include additional or fewer peripheral fixation members 16.

The articular surface 20 is configured to partially receive and nestingly engage or articulate with the humeral head. For example, the articular surface 20 can be patient-specific and can have a concave hemispherical shape that closely conforms as mirror-image or negative or a complementary surface of the humeral head. The humeral head can be part of a natural humerus of a specific patient, or the humeral head can be part of a humeral implant. A 3D model of the humeral head can be obtained using an x-ray, MRI, CT, ultrasound or other medical scan, and the articular surface 20 can be designed (e.g., shaped, sized, contoured) based on the 3D model. If the humeral head is part of a humeral implant, the 3D model can be obtained from the CAD files used to design the humeral implant.

The scapula-engaging surface 22 may include a plurality of protrusions or teeth 23 extending therefrom. The teeth 23 may be shaped as pyramidal frustums, for example. In one configuration, the teeth 23 may be shaped as truncated square pyramids. The teeth 23 may be arranged in a grid or array of orthogonally disposed rows, helping bone cement to flow or otherwise disburse between the bone and the bone-engaging side.

The central fixation member 14 and/or the peripheral fixation members 16 can be formed integral with the body 12 or separate from the body 12. In one example, the peripheral fixation members 16 can be formed integral with the body 12, and the central fixation member 14 can be formed separate from the body 12 and press fit or threaded into a blind hole in the body 12. The blind hole can be formed in a domed portion 24 (FIG. 3) of the body 12 that extends from the scapula-engaging surface 22. In this regard, the implant 10 can also include an internally-threaded insert 25 that is disposed, and otherwise secured within (e.g., press-fit, adhesive, mechanical fasteners, etc.) the blind hole. The insert 25 can be formed from a metallic, or other similar high strength material, thus helping to ensure that the central fixation member 14 is securely coupled to the insert 25 and the body 12. The central fixation member 14 may be formed from a biocompatible material, such as a porous metallic material. For example, in some configurations, the central fixation member 14 may include, or otherwise be formed from, a porous titanium material such as REGENEREX®, or OSSEOTI®, both of which are commercially available from Biomet Manufacturing Corporation. The porous metal material of the central fixation member 14 can allow for the ingrowth of bone into the central fixation member 14, thereby improving the fixation of the central fixation member 14 and the implant 10 relative to the glenoid or other bone.

The central fixation member 14 may be substantially similar to the "central peg 14" found in commonly owned U.S. patent application Ser. No. 14/095,565. In this regard, the central fixation member 14 includes a first portion 26, a second portion 28 that extends from the first portion 26, a third portion 30 that extends from the second portion 28, and a fourth portion 32 that extends from the third portion 30. The first, second, and third portions 26, 28, and 30 can be cylindrical and concentric, and the fourth portion 32 can be a rectangular cube or another non-cylindrical shape for receipt in a drive tool such as a socket. In this regard, it will be appreciated that while the fourth portion 32 is illustrated and described as extending from the third portion 30, the fourth portion 32 may alternatively include a divot or recessed portion (not shown) formed in the fourth portion 32. The divot or recessed portion may similarly define a cubic, hexagonal, or non-cylindrically shaped void for receipt of a drive tool such as a screwdriver or Allen wrench. As shown in FIG. 3, the first portion 26 can have a first diameter D1, the second portion 28 can have a second diameter D2 that is less than the first diameter D1, and the third portion 30 can have a third diameter D3 that is less than the second diameter D2. Thus, the central fixation member 14 can decrease in diameter from the first portion 26 to the third portion 30 in a stepped manner, which may strengthen a press fit between the central fixation member 14 and a corresponding hole in the scapula. Alternatively, the diameter of the central fixation member 14 can be decreased in a tapered manner to strengthen the press fit.

Figure 5:
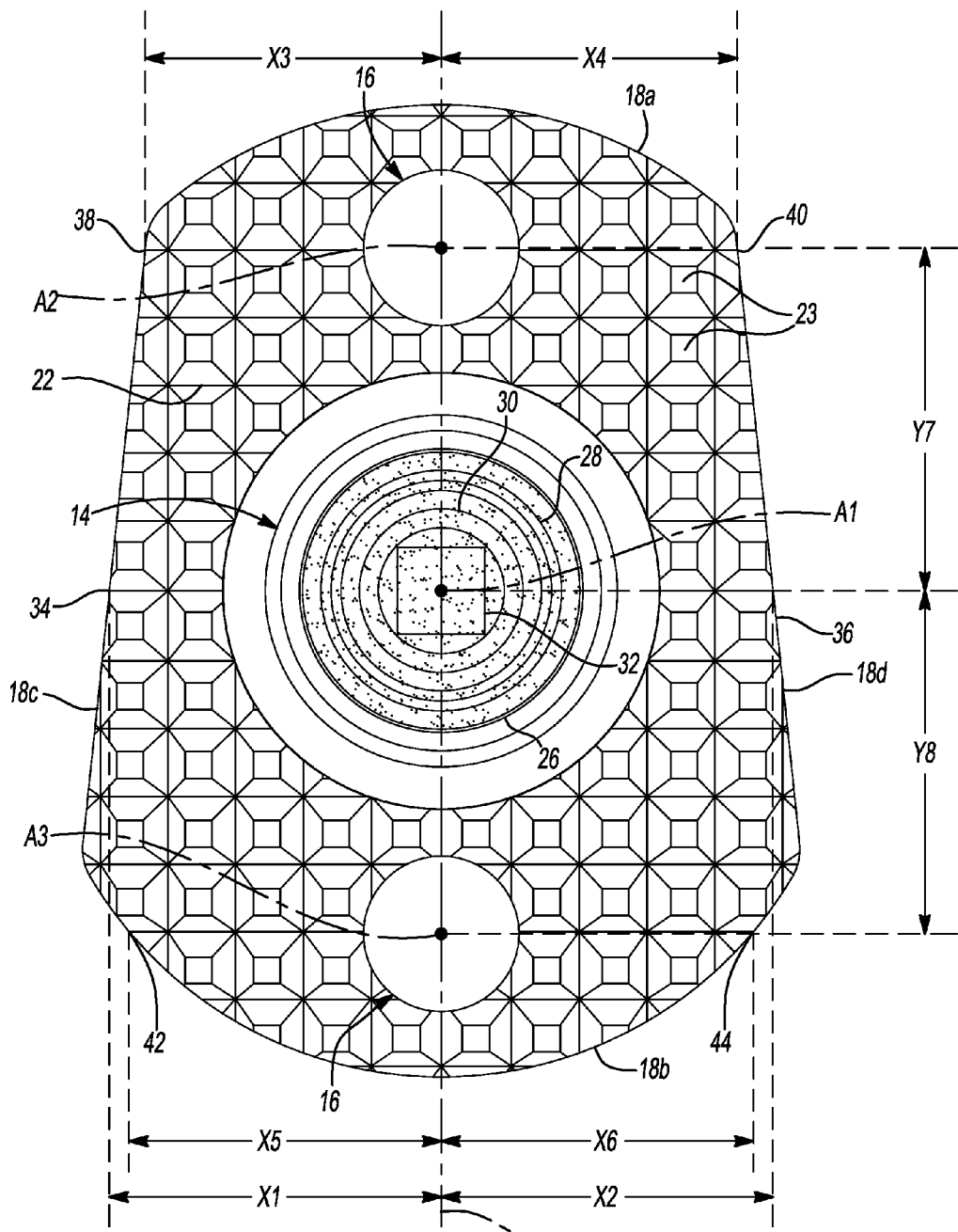
FIG. 5 is a front view of the glenoid implant of FIG. 1.

The central fixation member 14 may be located at a central portion or region of the scapula-engaging surface 22, relative to the superior and inferior portions 18a, 18b, and/or relative to the anterior and posterior portions 18c, 18d, of the peripheral surface 18. In this regard, as illustrated in FIG. 5, in some configurations a first laterally extending distance X1 between the central fixation member 14 and a first location 34 on the peripheral surface 18 may be substantially equal to a second laterally extending distance X2 between the central fixation member 14 and a second location 36 on the peripheral surface 18. The first location 34 may be aligned with the second location 36 relative to the longitudinal axis A of the body 12, such that a line extending from the first location 34 to the second location 36 intersects the first central axis A1. In this regard, in some configurations the distance X1 may extend from the anterior portion 18c to the first central axis A1, and the distance X2 may extend from the posterior portion 18d to the first central axis A1.

With continued reference to FIG. 5, the peripheral fixation members 16 may be located at a central portion or region of the scapula-engaging surface 22, relative to the anterior and posterior portions 18c, 18d of the peripheral surface 18. In this regard, in some configurations, a third distance X3 between the superior peripheral fixation member 16 and a third location 38 on the peripheral surface 18 may be substantially equal to a fourth distance X4 between the superior peripheral fixation member 16 and a fourth location 40 on the peripheral surface 18. The third location 38 may be aligned with the fourth location 40 relative to the longitudinal axis A of the body 12, such that a line extending from the third location 38 to the fourth location 40 intersects the second central axis A2. In this regard, in some configurations the third distance X3 may extend from the anterior portion 18c to the second central axis A2, and the fourth distance X4 may extend from the posterior portion 18d to the second central axis A2. Similarly, in some configurations, a fifth distance X5 between the inferior peripheral fixation member 16 and a fifth location 42 on the peripheral surface 18 may be substantially equal to a sixth distance X6 between the inferior peripheral fixation member 16 and a sixth location 44 on the peripheral surface 18. The fifth location 42 may be aligned with the sixth location 44 relative to the longitudinal axis A of the body 12, such that a line extending from the fifth location 42 to the sixth location 44 intersects the third central axis A3. In this regard, in some configurations the fifth distance X5 may extend from the inferior portion 18b to the third central axis A3, and the sixth distance X6 may extend from the inferior portion 18b to the third central axis A3.

The central fixation member 14 may be disposed between the peripheral fixation members 16 such that the superior peripheral fixation member 16 may be located a seventh distance Y7 from the central fixation member 14, and the inferior peripheral fixation member 16 may be located an eighth distance Y8 from the central fixation member 14. In this regard, the seventh distance Y7 may extend from and between the first and second central axes A1, A2, and the eighth distance Y8 may extend from and between the first and third central axes A1, A3. In some configurations, the seventh distance Y7 may be substantially equal to the eighth distance Y8. It will be appreciated, however, that the seventh distance Y7 may differ from the eighth distance Y8 within the scope of the present disclosure.

At least two of the central fixation member 14 and the peripheral fixation members 16 may be centrally located relative to the anterior and posterior portions 18c, 18d of the peripheral surface 18, such that the central longitudinal axis A intersects the central fixation member 14 and/or the peripheral fixation member(s) 16. As illustrated in FIG. 5, in some configurations, the central fixation member 14 may be disposed between the peripheral fixation members 16, such that the central fixation member 14 and the peripheral fixation members 16 define a substantially linear configuration along the central longitudinal axis A. As illustrated, the central longitudinal axis A may define an axis of symmetry of the scapula-engaging surface 22 and/or the implant 10.

It will be appreciated that the centrally located, linear configuration of the central fixation member 14 and/or the peripheral fixation members 16 can allow for the improved placement of the implant 10 in a glenoid having a narrow or otherwise small surface area. In this regard, the implant 10 is configured to be fixed to a scapula without using fixation hardware such as bone screws. For example, the central fixation member 14 and the peripheral fixation members 16 can be press fit into holes formed in a central portion of the glenoid cavity to fix the implant to the scapula. As discussed above, the porous construct of the material forming the central fixation member 14 can allow for the ingrowth of bone into the central fixation member 14, further improving the fixation of the central fixation member 14 and the implant 10 relative to the glenoid or other bone. In addition, annular grooves 46, defining fins or flanged portions 48, can be formed in the peripheral fixation members 16 for receiving bone cement to fix the peripheral fixation members 16 within corresponding holes in the scapula. In this regard, in some configurations the peripheral fixation members 16 may include an annular fin (not shown) substantially similar to the "annular fin 40" found in commonly owned U.S. patent application Ser. No. 14/226,051 filed Mar. 26, 2014 and entitled "Press-Fit Glenoid with Peripheral Compression Pegs", which is hereby incorporated by reference in its entirety.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A glenoid implant, comprising:
    a body having a pear-shaped outline including an articular surface and a scapula-engaging surface opposite from the articular surface, the body at least partially formed from a polyethylene material, the scapula-engaging surface including a plurality of teeth extending therefrom and arranged in an array of orthogonally disposed rows;
    an internally-threaded insert secured within a blind hole located in the body at a central portion of the scapula-engaging surface, the insert secured to said blind bore by mechanical fasteners or an adhesive;
    a first fixation peg extending from the scapula-engaging surface and including a radially-extending flange;
    a second fixation peg extending from the scapula-engaging surface and including a radially-extending flange; and
    a third fixation peg configured to extend from the central portion of the scapula-engaging surface and threadably connect to the insert, the third fixation peg including a porous titanium material and being disposed between the first and second fixation pegs, such that the first, second and third fixation pegs define a substantially linear configuration,
    wherein the third fixation peg includes a stepped outer surface including a first portion, a second portion, a third portion, and a fourth portion, the first portion, the second portion, and the third portion each being cylindrical and having a diameter that differs from one another, the fourth portion having a non-cylindrical shape sized to receive a drive tool,
    wherein the first portion is connected to the second portion by a first tapered portion, and the second portion is connected to the third portion by a second tapered portion,
    wherein at least a portion of the body is a patient-specific surface configured to mirror and conform to a surface of a glenoid cavity of a patient.

2. The glenoid implant of claim 1, wherein the substantially linear configuration defines a central axis relative to the scapula-engaging surface.

3. The glenoid implant of claim 1, wherein the third fixation peg is removably coupled to the glenoid implant.

4. The glenoid implant of claim 1, wherein at least one of the first and second fixation pegs includes the polyethylene material.

5. The glenoid implant of claim 1, wherein the polyethylene material includes an antioxidant.

* * * * *